(12) United States Patent
Jaross et al.

(10) Patent No.: US 6,577,891 B1
(45) Date of Patent: Jun. 10, 2003

(54) IR SPECTROSCOPIC ENDOSCOPE WITH INFLATABLE BALLOON

(75) Inventors: Werner Jaross, Rabenau (DE); Matthias Boese, Karlsruhe (DE); Arno Simon, Karlsruhe (DE)

(73) Assignee: Bruker Optik GmbH, Ettlingen (DE)

( * ) Notice: Subject to any disclaimer, the term of this patent is extended or adjusted under 35 U.S.C. 154(b) by 0 days.

(21) Appl. No.: 09/466,299

(22) Filed: Dec. 17, 1999

(30) Foreign Application Priority Data

Dec. 22, 1998 (DE) .......................... 198 59 434

(51) Int. Cl.⁷ .................................. A61B 6/00

(52) U.S. Cl. .................. 600/473; 600/478; 600/116; 604/101.01; 604/102.02; 606/192; 606/15

(58) Field of Search .................. 604/104, 915, 604/916; 600/101–183, 473–480

(56) References Cited

U.S. PATENT DOCUMENTS

| | | | |
|---|---|---|---|
| 5,114,423 A | | 5/1992 | Kasprzyk et al. |
| 5,318,024 A | * | 6/1994 | Kittrell et al. ............. 600/478 |
| 5,549,555 A | * | 8/1996 | Sohn .................... 604/101.01 |
| 6,016,440 A | * | 1/2000 | Simon et al. ............. 600/160 |
| 6,110,106 A | * | 8/2000 | MacKinnon et al. ........ 600/160 |

FOREIGN PATENT DOCUMENTS

DE 197 32 215 A1 2/1998

OTHER PUBLICATIONS

Pschyrembel Klinisches Wörterbuch (Pschyrembel clicical encyclopedia), pp. 170–171, 530–531, 622–623, 1536–1537.

* cited by examiner

*Primary Examiner*—Marvin M. Lateef
*Assistant Examiner*—Barry Pass
(74) *Attorney, Agent, or Firm*—Paul Vincent

(57) ABSTRACT

A device for the optical spectroscopic examination of interior surfaces (2, 2') of a body, e.g. of blood vessels (1), comprising an optical spectrometer and an endoscope (3) with a light guide for illuminating the surfaces, wherein at the proximal end of the light guide it is supplied with light and at the distal of the light guide the light can be launched to the surfaces to be examined, wherein at the distal end of this endoscope there is provided a device for receiving the light reflected by the surfaces to be examined, is characterized in that the distal end of the light guide is arranged within an inflatable balloon (4) with an elastic exterior, and that the light decoupled from the light guide and the light reflected by the surfaces to be examined to the receiving device penetrates in each case the exterior of the balloon. In this way, the light launched by the light guide and also the light directed to the surface to be examined and the light scattered by them, if e.g. interior walls of the vessels in the human body are to be examined, does not pass twice a layer of blood or body fluid, and the distal end of the endoscope is fixed such that during measurements, shaking and change of relative distances can be largely avoided, whereby the quality at the received optical spectra is considerably improved.

2 Claims, 4 Drawing Sheets

IR SPECTROSCOPIC ENDOSCOPE WITH INFLATABLE BALLOON

This application claims Paris Convention priority of German patent application 198 59 434.8 filed Dec. 22, 1998, the complete disclosure of which is hereby incorporated by reference.

BACKGROUND OF THE INVENTION

The invention concerns a device for the optical-spectroscopic examination of interior surfaces of a body, e.g. of blood vessels, comprising an optical spectrometer and an endoscope with a light guiding means for the illumination of surfaces, wherein light is guided into the light guiding means at its proximal end and at its distal end the light is launched at the surfaces to be examined, wherein the distal end of the endoscope comprises a means for receiving the light reflected by the surfaces to be examined.

A device of this type is known in connection with an infrared (=IR) spectrometer from DE 197 32 215 A1, wherein reference is made to the said complete document.

With endoscopes of this type, scattered light is guided from interior surfaces of a body, mainly from blood vessels or cavities inside the body, via light guides to an external detector to the outside. Usually glass fiber bundles are used as light guides. As an alternative, also NIR transparent materials like silver hologenides or chalcogenides can be used. The intensity of the scattered light received and thus the signal intensity of the signal received is mainly proportional to the product of the cross-sections of the fibers, which guide the light from the spectrometer through the endoscope for recording, and of the cross sections of those fibers would receive the scattered light and guided outside to the detector.

A disadvantage of an endoscope of this type consists in that on the one hand the light directed to the surfaces to be examined, if. e.g. the inner vascular walls in a human body are to be examined, has to pass at first from the distal end of the light guiding means through the blood or other body fluids to the surface to be examined, and that the light reflected or scattered from there, has to penetrate the corresponding fluid again on its way back to the endoscope, said fluid normally being in motion, such that the local density may change with time. A further disadvantage consists also in that the distal end of the endoscope is not fixed, and thus shaking and a change of relative distances may happen during measurements, thus reducing the quality of the recorded optical spectra.

SUMMARY OF THE INVENTION

In contrast thereto, it is the object of the present invention to improve a device of the initially defined type in as simple as possible manner to obviate the above-mentioned disadvantages.

According to the invention, this object is achieved in a both simple and effective manner in that the distal end of the light guiding means is arranged within an inflatable balloon with an elastic exterior and that the light launched at the light guiding means and also the light reflected from the surfaces to be examined to the recording device penetrates in each case the exterior of the balloon.

Inflation of the balloon at the distal end of the light guiding means causes displacement of body fluids and of flowing blood and the exterior of the balloon abuts in a fixing manner in the area of the vascular inner wall to be examined such that the distal end of the endoscope does no longer change its relative distance from the surrounding wall of the vessel in the inflated state of the balloon. Thus, outer influences that change with time and might have a disadvantageous effect on the quality of the spectra are eliminated.

Inflatable balloon catheters as such are known in general, e.g. from "Pschyrembel Klinisches Wörterbuch", Walter de Gruyter-Verlag, Berlin, N.Y., 1986, pages 170, 531, 622 and 1536. These known balloon catheters are, however, not used in connection with optical spectrometers. Their mechanical and optical construction is thus not suited to be used with a device according to the present invention.

One embodiment of the inventive device is preferred, wherein the elastic exterior comprises transparent sections in the area where the light enters and exits. In this way it is possible to optimize the elastic properties of the exterior of the balloon on the one hand and their optical properties in the area of the interesting surfaces on the other hand, independently of one another.

It is e.g. feasible to insert transparent "windows" in the corresponding sections of the exterior of the balloon. However, one embodiment is preferred in which the material of the elastic exterior is selected such that it is largely transparent in the spectral range of interest. In this manner, the light used for the spectroscopic examination may theoretically penetrate the exterior of the balloon unhindered at any point and it is not required to insert transparent sections under great efforts, but the exterior of the balloon can be produced of one piece.

In further embodiments of the invention, the elastic exterior of the balloon may preferably be formed of latex material which is known to be medically well compatible, has been tested for decades and is readily available. At least if the thickness of the exterior of the balloon is small, it is possible to achieve sufficient transparency in a large wavelength range.

In a particularly preferred manner, the balloon can be inflated with inert gas, preferably with helium. The path of rays in the direction of the surfaces to be examined and also away from the surfaces towards the detector extends in a chemically inert, optically highly transparent homogeneous medium.

In a particularly preferred embodiment of the device according to the invention, the elastic exterior of the balloon is constructed in such a manner that, in its inflated state, a cross-section of passage of a blood vessel to be examined remains open. In this manner, the passage of blood during vascular examinations can be maintained at least to a limited degree which may be vital with certain blood vessels.

In an advantageous further development of this embodiment, the exterior of the inflated balloon has at least one radial recess in its cross-section along the entire axial extent of the balloon which produces a cross-section of passage outside of the exterior of the balloon.

This further development is particularly easy to realize in that the exterior of the balloon in the area of the recess is formed of a thicker, reinforced and/or stiffened material. When the balloon is inflated, the exterior in this area will remain essentially rigid such that the desired recess will be formed there.

In an alternative further development, a continuous hollow channel extends along the axis of the endoscope through the elastic exterior of the balloon thus maintaining a defined and constant cross-section of passage through the balloon.

This is achieved in a particularly preferred manner by disposing the hollow channel on the axis of the endoscope and arranging the elements of the light guiding means, in particular optical fibers, in a circle around the hollow channel. This geometrical arrangement does not restrict the field of view of the endoscope. Despite the hollow channel it is possible to examine 360° of the surrounding surfaces in an annular view.

One embodiment of the device according to the invention is also advantageous in which the distal end of the light guiding means can be displaced relative to the exterior of the balloon, preferably in the direction of the longitudinal axis of the endoscope.

With a stationary endoscope, it is still possible to obtain recordings with longitudinal local dependency.

In a particularly preferred embodiment, the illuminated distal end of the light guiding means is provided with an ultrasound head which is rotatable preferably about the longitudinal axis of the endoscope. In this manner, critical locations, e.g. vascular constrictions can be pre-localized through ultra sound images and can subsequently be examined by an infrared spectroscope which images may serve e.g. for identifying the type of tissue or for analyzing depositions.

The light guiding means in embodiments of the invention may comprise one or more fiber bundles which have been available on the market for many years.

In a preferred further development of these embodiments, the distal end of the light guiding means is provided with means for deflecting the light by approximately 90°. In this way it is possible to illuminate an area to be examined which is transverse to the longitudinal axis of the endoscope as it is typically the case with blood vessels.

The deflection may be effected via a preset mirror or via a prism disposed onto the fiber bundle.

In a further development which is particularly easy to produce and thus cheap, the fiber ends themselves are chamferred altogether in the form of a prism at an angle of approximately 45°. The deflection of the light is effected by total reflection or by disposing mirrors on the chamferred surface.

In embodiments, the spaces between the fibers of the fiber bundle in the area where the light exits are filled with a material which has a refractive index in the IR spectral range of interest such that the refractive index difference between the fiber and material is small enough to transmit the IR light which comes in at an almost perpendicular angle and is reflected from the chamferred fiber ends.

In this manner, the light bundles emitted by a central fiber may penetrate the edge fibers largely without any loss of reflection.

To ensure the guidance of the IR light in the fibers, the fiber surfaces outside of the area where the light exits, may be lined with mirrors.

A particularly easy further development of the invention is characterized in that the means for deflecting the IR light are formed by abrading the ends of the optical fibers in a plane manner perpendicularly to the longitudinal axis of the endoscope, and by arranging mirrors in an axial direction behind the optical fiber ends at the distal end of the endoscope.

In this connection, the mirror arrangement may comprise a parabolic mirror which enables the generation of a parallel beam.

The mirror arrangement may also comprise an elliptical mirror, whereby the ends of the light guiding means where the light exits, can be reproduced in a focussing manner.

One variant is particularly easy in which the mirror arrangement comprises a plane mirror such that a simple non-reproducing deflection of the beams is effected.

In embodiments of the inventive device, the light guiding means may supply light for irradiating the surface to be examined as well as return light received from the surface to a detector as it is the case with most endoscopic arrangements.

A further development of this embodiment is characterized in that the fiber bundles are formed, in each case, of a central afferent fiber which guides light in the direction towards the surface to be examined, and of several efferent fibers which are arranged in circles around the central fiber and return light from the surface to the detector. In this manner, the useful cross-section of the endoscope is utilized to an optimum degree.

One variant of this embodiment is of particular advantage in which the fiber bundles are arranged on the inside of a surrounding exterior in the form of a circle.

The spectrometer may also be a Raman spectrometer. Illumination of the surfaces to be examined is effected by monochromatic light of high intensity. The Raman effect measured offers information which is complementary to the usual absorption or reflection spectrometry. Furthermore, it can be used to observe information from a totally different spectral range.

Embodiments of the device according to the invention are particularly preferred in which the optical spectrometer is an infrared (=IR), in particular a near infrared (=NIR) spectrometer. Infrared spectrometry is probably one of the main applications of optical endoscopes of this type in the medical field. For this purpose, glass fibers for the light guiding means which are optimized in the infrared wavelength range are available in a wide variety.

One further development of this embodiment is preferred, wherein the IR spectrometer is a Fourier spectrometer with an interferometer which converts the signals coming from the surface to be examined into an interferogram and by means of Fourier transformation into an IR spectrum. In this way, it is possible to achieve shorter measuring times and improved light intensities.

In a further development, the light guided into the light guiding means at the proximal end of the endoscope is launched by the IR spectrometer. This allows particularly easy connection of the endoscope to commercial IR spectrometers.

One further development is particularly preferred, wherein the distal end of the light guiding means comprises a detector for receiving and converting IR light scattered on the illuminated surface, into electric signals. An arrangement of this type is known from the initially cited DE 197 32 215 A1 to the full contents of which is referred to again and the further developments of which can be combined without any problems with the basic idea of the present invention. This arrangement, which is known per se, in connection with the device according to the invention improves the signal strength and thus additionally enables reduction of the measuring time thus maintaining the same signal quality.

In a preferred further development, the light-sensitive surface of the detector is mounted directly on an outer surface of the light guiding means. In this manner, the detector does practically not require additional space and the endoscope of the inventive device can be constructed in a particularly compact manner.

One embodiment is particularly preferred in which the distal ends of the fibers of the fiber bundle are arranged in a circle on the inner wall of a detector which is also of annular shape.

This arrangement itself without the features of the inventive device mentioned above, offers great advantages in itself, and particularly high light penetration through the endoscope. The exiting light does not have to penetrate any filling material or other fibers of the light guiding means. In this manner it is possible to avoid complicated geometrical configurations of the light guiding fibers.

In a particularly preferred variant of the inventive device, the sensitive surface of the detector in the peripheral direction of the endoscope is constructed in lateral segments. This enables locally-resolved measurements without any problems if the signals from the individual detector segments are processed separately.

In this connection, it is again particularly advantageous to associate each detector segment with at least one unique fiber illuminating the surface to be examined.

In another further development, which can be realized in a particularly advantageous manner in combination with the above further development, each fiber is supplied with light separately. In this manner, it is possible to produce an information matrix from the signals of the surfaces to be examined which enables a considerably better local resolution.

A method of operating a device of the above-mentioned type lies also within the scope of the present invention in which the fibers are supplied with light in the time multiplex to obtain a corresponding locally-resolved spectrum.

As an alternative or supplement, in a further variant of the method the signals received in the detector segments can be read out in the time multiplex. In this way it is possible to achieve an even better local resolution of the spectra.

Further advantages of the invention can be gathered from the description and the drawing. The features mentioned above and below may be used according to the invention individually or collectively in any arbitrary combination. The embodiments shown and described are not to be understood as exhaustive enumeration but rather have exemplary character for describing the invention.

The invention is shown in the drawing and further explained by means of embodiments. In the drawing:

BRIEF DESCRIPTION OF THE DRAWING

FIG. 3b shows a section along the line A—A in FIG. 3a;

FIG. 4b shows a cross-sectional view in the direction X of the embodiment according to FIG. 4a.

DESCRIPTION OF THE PREFERRED EMBODIMENT

Figure 1A:
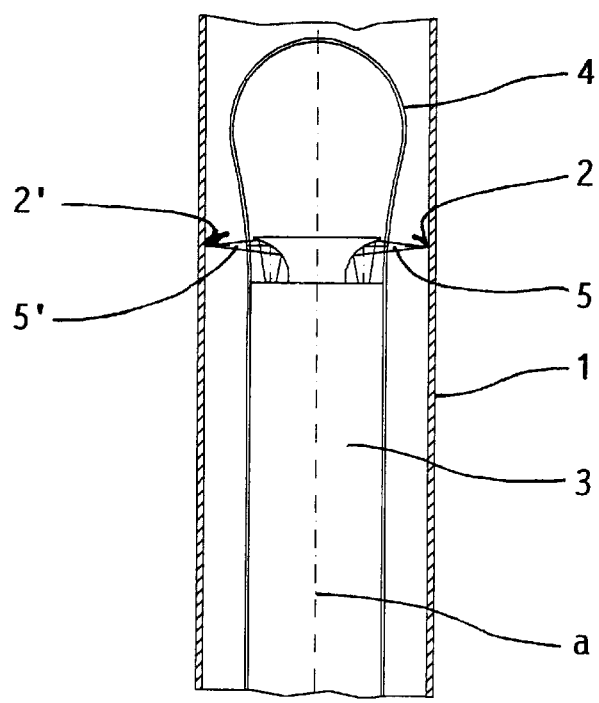
FIG. 1a shows a schematic longitudinal section through the distal end of the endoscope of an embodiment of the inventive device within a vessel to be examined, wherein the balloon is not inflated.

The distal end of the device according to the invention, as shown in FIG. 1a in a highly schematic manner in relation to a vascular wall 1, the interior surfaces 2, 2' of which are to be examined, comprises at the distal end of an endoscope 3 an inflatable balloon 4 with an elastic exterior surrounding the endoscope 3. It is possible to guide light 5, 5' through this elastic exterior from a light guiding means of the endoscope 3, explained in more detail below, to the surfaces 2, 2' to be examined.

Figure 1B:
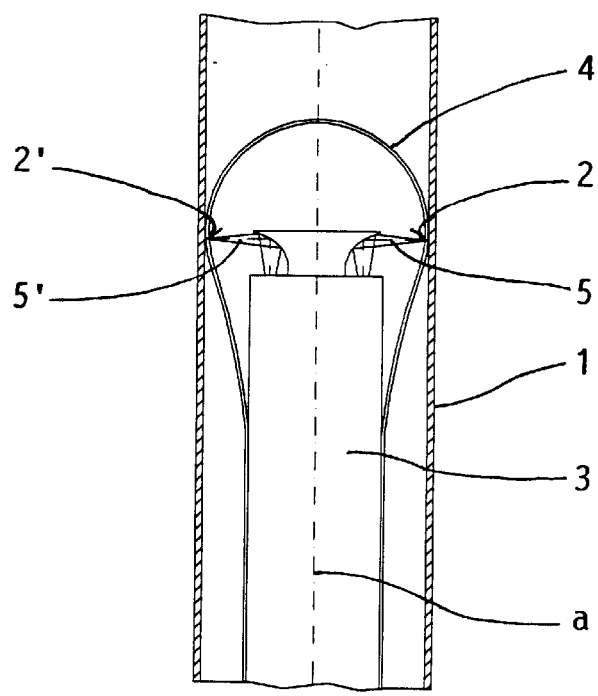
FIG. 1b shows the same as FIG. 1a, wherein, however, the exterior of the balloon is inflated.

In FIG. 1b, the exterior of the balloon 4 is shown in the inflated state such that the balloon 4 lies tightly on the inner walls of the vessel 1. In this manner, shaking of the distal end of the endoscope 3 is prevented. The light reflected by the surfaces 2, 2' to be examined penetrates again the elastic exterior of the balloon 4 and is guided to a detector as explained in more detail below.

The distal end of the inventive device corresponds to a balloon dilatation catheter (over the wire, monorail, fixed wire, single-operator-exchange type etc.), comprising a light guiding means inside. The light guiding means may e.g. be introduced into the catheter through a lateral opening and pushed forward into the centre of the balloon 4.

The point of entry of the light guiding means might be provided close to end of the catheter facing away from the blood vessel, such that the light guiding means does not get in direct contact with a patient and thus can be used several times. The balloon 4 is pumped up with helium through the catheter such that a volume filled with gas and the exterior of the balloon 4, which may consist of latex material, are located between the light guiding means and the vascular inner wall 2, 2'. The gas pressure in this case should be only slightly above the systolic blood pressure (approximately 300 hPa) in order to displace the blood completely from the space between the balloon 4 and the vessel 1 without inducing inflammatory reactions. A guiding wire, not shown in the drawing, is pulled back before the spectroscopic measurement that far that the illumination of the tissue to be examined is not limited.

Figure 2A:
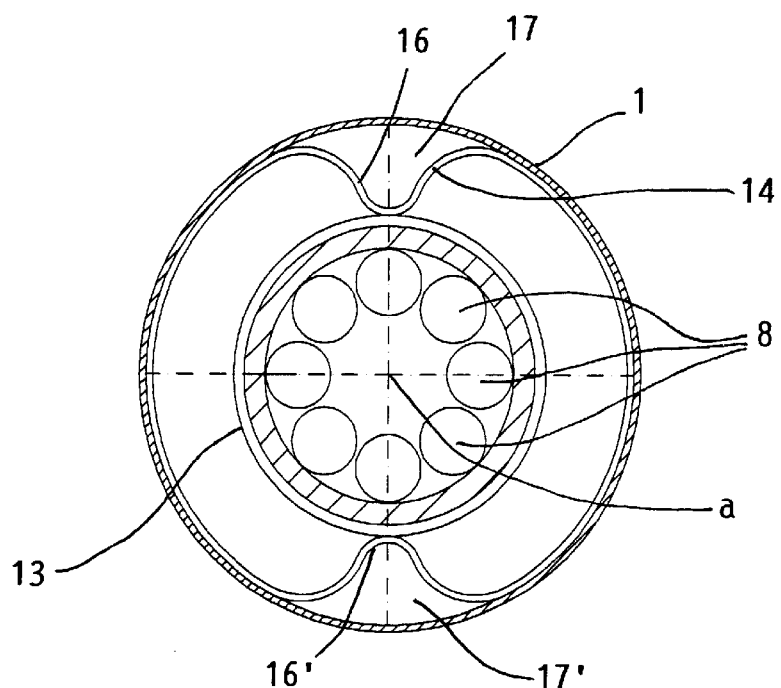
FIG. 2a shows a schematic sectional representation perpendicular to the axis of the endoscope at the level of the exterior of the balloon in the inflated state, of an embodiment with a recessed outside for opening a cross-section of passage.
Figure 2B:
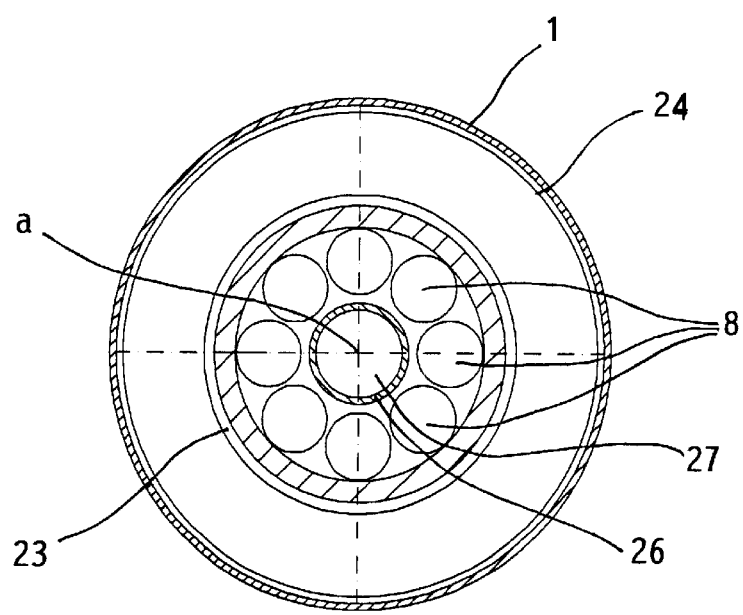
FIG. 2b shows a schematic section perpendicular to the axis of the endoscope in a further embodiment with a hollow channel extending through the balloon.

FIGS. 2a and 2b show two embodiments of the device according to the invention in a schematic cross-section perpendicular to the axis a of the endoscope. In both cases, there remains in each case a cross-section of passage 17,17';27 even in the inflated state of the balloon 14 through which e.g. blood may flow into the vessel 1.

In the embodiment according to FIG. 2a, the open cross-section of passage 17,17' is kept open by a recess 16,16' in the exterior of the balloon 14 in each case. This recess 16,16' may be formed in the simplest way by reinforcing or rigidifying the material of the balloon 14 in this area such that the exterior of the balloon is not deformed in this area during inflation. The balloon 14 does not lift off from the wall 13 of the endoscope during inflation, which wall again surrounds elements of a light guiding means 8.

In the embodiment according to FIG. 2b, a free cross-section of passage 27 is achieved in that a hollow channel 26 passes through the exterior of the balloon 24. In the inflated state of the balloon 24, thus the entire exterior may be lifted off completely from the wall 23 of the endoscope.

The light guiding means 8 is to enable the spectroscopic analysis of the vascular inner wall. It consists in general of bundled fibers which are suitable for spectroscopic applications which direct the light used, in most cases near infrared (NIR) light from a spectrometer, not shown in the drawing, at the proximal end of the endoscope 3 to the vessel 1 at the distal end of the endoscope 3 and return the light scattered by the vessel 1 to a detector.

Figure 3A:
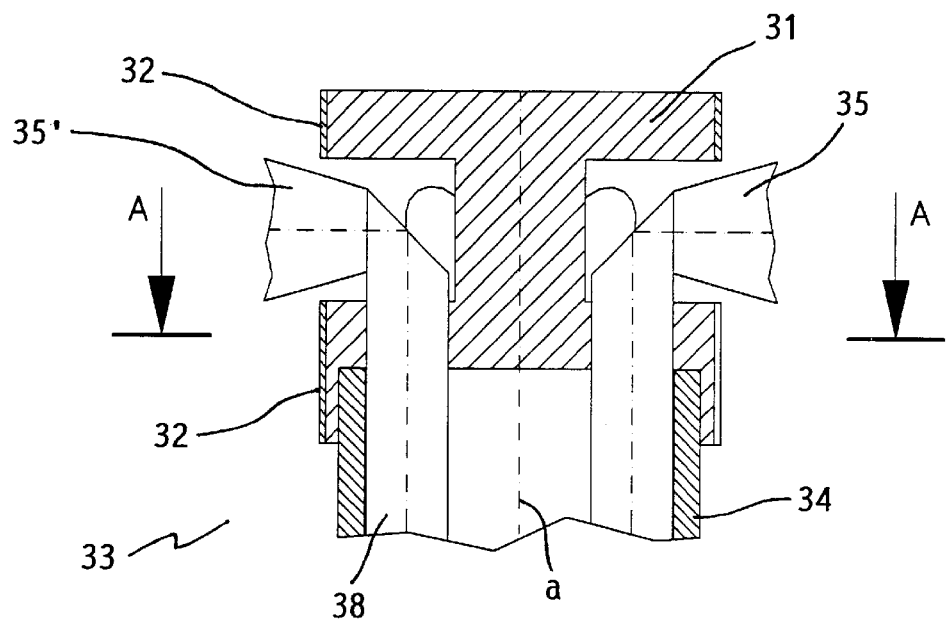
FIG. 3a shows a longitudinal section through the distal end of the endoscope, in an embodiment in which a detector is integrated.
Figure 3B:
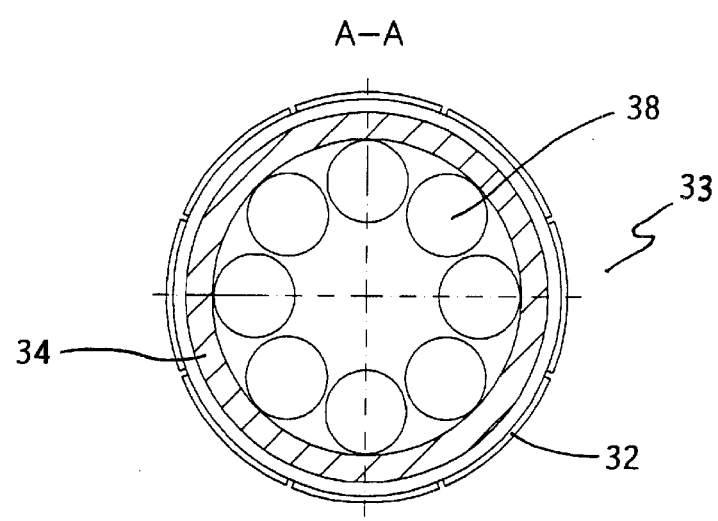

FIGS. 3a and 3b show an embodiment wherein a detector 31 comprising a light-sensitive layer 32 is disposed at the proximal end of the endoscope 33 not shown in the drawing.

The cross-sectional surface of the endoscope 33 which is available, is filled by the individual fibers 38 which are arranged in a circle and guide the IR light from the spectrometer to the vessel 1. The distal fiber ends are chamferred in the form of a prism at an angle of approximately 45° such that the light 35,35' coming from the spectrometer is deflected by approximately 90° —in the direction of the interior wall of the vessel. The deflection of light is achieved either by total reflection or by arranging mirrors on the chamferred surfaces at the fiber ends. As an alternative to the chamfering of the fibers 38 it is possible to glue prisms onto the individual fibers.

The light 35,35' deflected by the fibers 38 exits through an annular diaphragm surrounding the outer surface 34 of the light guiding means which is surrounded proximally and distally by the tube-shaped detector surface, the IR light-sensitive layer 32 of which is disposed on the outside.

The detector surface is divided such that the area above and below a fiber end belongs to one element in each case. This division of the detector 31 into segments 31 enables a locally resolved IR spectroscopic measurement of the interior wall of the vessel at a radius of 360° about the fiber probe head without having to turn the light guiding means within the catheter. The electric signals registered at the individual detector elements may be guided to the spectrometer either through guiding strips disposed outside of the outer surface 34 or through wires in the centre of the light guiding means. To guarantee guidance of the signal without disturbances also with low signal intensities, the signal should be digitized already in direct proximity of the detector 31.

Since the embodiment shown in FIGS. 3a and 3b does not require any space for returning fibers, it is possible to guide more light to the vessel 1 through the same endoscope cross-section as compared with common devices with external detector.

Figure 4A:
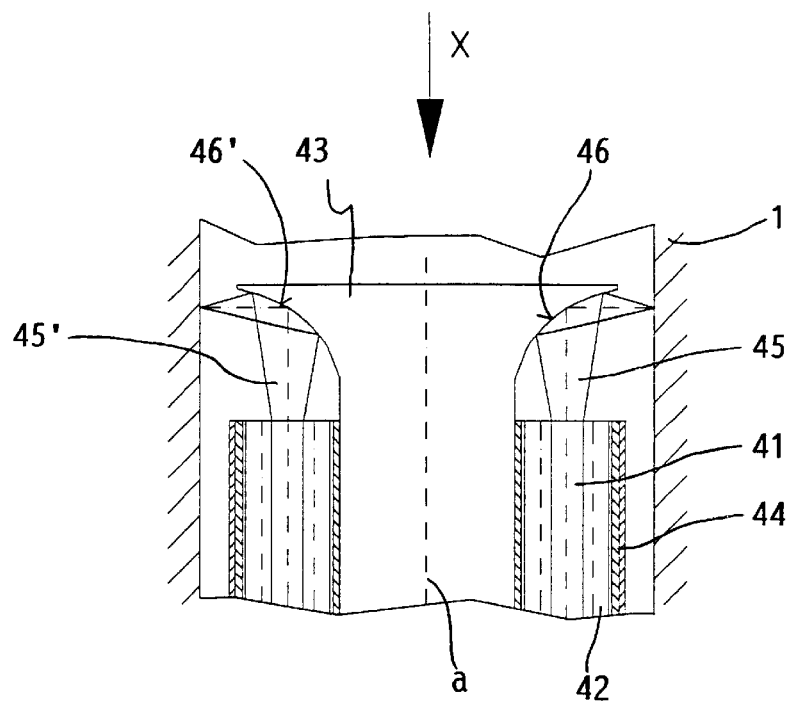
FIG. 4a shows a schematic longitudinal section through the distal end of the endoscope in an embodiment with fiber bundles of the light guiding means, wherein circular efferent fibers are arranged in each case about a central afferent fiber.
Figure 4B:
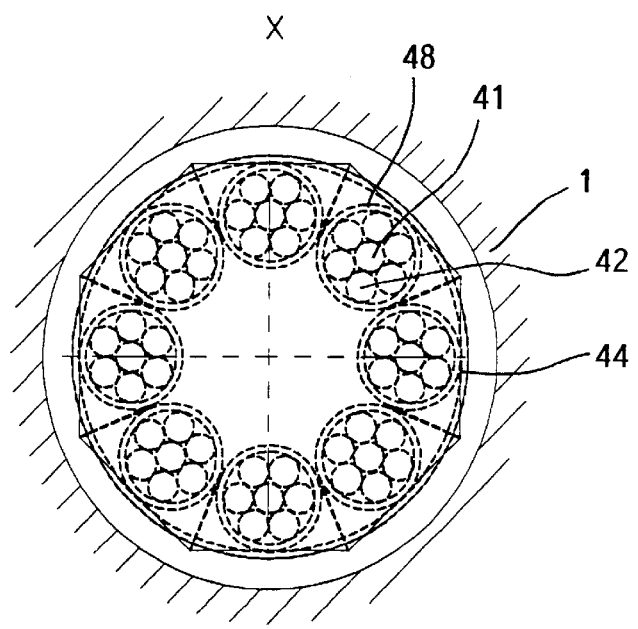

In order to achieve an optimum signal intensity, the cross-sectional surface of the endoscope 43 available in the embodiment shown in FIGS. 4a and 4b, is filled with fiber bundles 48 arranged in a circle.

In the fiber bundles 48 central afferent individual fibers 41 guiding light are surrounded in each case by six efferent individual fibers 42 returning light (6+1 fiber bundle). The fiber bundles 48 again are arranged in a circle in the inner side of a surrounding exterior 44.

The light 45,45' emitted in the longitudinal direction of the afferent individual fibers 41 is reflected via one or more distally arranged mirrors 46,46' onto the wall 1 of the vessel. By means of elliptical mirrors the outlet opening of the individual fibers 41 can be reproduced on the interior surface of the vessel 1. As an alternative, it is possible to use parabolic mirrors (light beam is converted into a parallel beam) or plane mirrors (light beam is deflected by approximately 90° as before).

Part of the light diffusely scattered or reflected at the tissue is reflected by the mirrors 46,46' to the fiber bundles 48 and guided by the efferent fibers 42 surrounding the afferent individual fibers 41 to the detectors located in the IR spectrometer. Since each individual fiber bundle is connected with a separate detector, one obtains several IR spectra with each measurement which are correlated in each case with a locally resolved section of the vascular interior wall surrounding the fiber probe head. As an alternative, also a more time-consuming successive read-out with one single detector is feasible.

It is possible to measure the interior wall of the vessel at a radius of 360° about the fiber probe head without turning the light guiding means within the catheter. For detecting the next vascular area, the gas is released from the balloon 4, the catheter is displaced and the balloon 4 is inflated again.

The individual mirrors 46,46' are interconnected or produced from one part to increase the stability. A central projection of the whole mirror composed of the individual mirrors projects distally into the central hollow space formed by the fiber bundles 48 and is glued therein with the surrounding fiber bundles 48 to be fixed.

We claim:

1. Device for the IR spectroscopy of interior surfaces (2, 2') of a body within a spectral range of interest comprising an optical spectrometer and an endoscope (3; 33; 43) with an IR light guiding means (8) for illuminating the surfaces (2, 2'), at the proximal end of which, IR light is guided into the IR guiding means (8) and at the distal end of the IR light guiding means the light can be launched at the surface (2, 2') to be examined, wherein at the distal end of the endoscope (3; 33; 43) a means for receiving IR light reflected by the surfaces (2, 2') to be examined is provided, characterized in that the distal end of the IR light guiding means (8) is arranged within an inflatable balloon (4; 14; 24) consisting essentially of an elastic exterior made from a substantially uniform, single material that is largely transparent in said spectral range of interest, and that the IR light launched from the IR light guiding means (8) as well as the IR light reflected by the surfaces (2, 2') to be examined can each penetrate the exterior of the balloon (4; 14; 24) independent of locations of their points of incidence thereon, wherein the elastic exterior of the balloon (4; 14; 24) is formed such that in the inflated state a cross-section for the passage (17; 17'; 27) of blood (1) to be examined remains free, with the elastic exterior of the balloon (14) being formed such that, in the inflated state, there is at least one radial recess (16, 16') in the cross-section through the entire axial extent of the balloon (14), wherein the exterior of the balloon (14) in the area of the recess (16, 16') is formed of a thicker, reinforced and/or rigidified material.

2. Device according to claim 1, characterized in that a continuous hollow channel (26) is guided along the axis (a) of the endoscope through the elastic exterior of the balloon (24).

* * * * *